(12) United States Patent
Nakayama et al.

(10) Patent No.: US 7,417,108 B2
(45) Date of Patent: Aug. 26, 2008

(54) PROCESS FOR PRODUCTION OF 2,3,3',4'-BIPHENYLTETRACARBOXYLIC DIANHYDRIDE

(75) Inventors: Tatsushi Nakayama, Ube (JP); Takeshi Matsuzaki, Ube (JP); Kenichiro Sasaki, Ube (JP)

(73) Assignee: Ube Industries Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 11/208,823

(22) Filed: Aug. 22, 2005

(65) Prior Publication Data

US 2006/0247445 A1 Nov. 2, 2006

(30) Foreign Application Priority Data

Apr. 28, 2005 (JP) ............................ 2005-130795

(51) Int. Cl.
*C08G 69/26* (2006.01)
*C07C 65/00* (2006.01)

(52) U.S. Cl. ....................... 528/353; 562/888
(58) Field of Classification Search .................... 562/4; 528/353; 560/154
See application file for complete search history.

(56) References Cited

U.S. PATENT DOCUMENTS 4,958,002 A * 9/1990 Imatani et al. ............... 528/353
5,047,560 A * 9/1991 Shoji et al. .................. 549/241

* cited by examiner

*Primary Examiner*—Paul A Zucker
(74) *Attorney, Agent, or Firm*—Knobbe Martens Olson & Bear LLP (57) ABSTRACT

A process for producing 2,3,3',4'-biphenyltetracarboxylic dianhydride (a-BPDA), comprising dehydrating 2,3,3',4'-biphenyltetracarboxylic acid in an inert gas atmosphere under heating at 180 to 195° C. is disclosed. This process produces high-purity a-BPDA which is suitable for production of a polyimide.

17 Claims, 3 Drawing Sheets

PROCESS FOR PRODUCTION OF 2,3,3',4'-BIPHENYLTETRACARBOXYLIC DIANHYDRIDE

CROSS-REFERENCE TO RELATED APPLICATIONS

This application claim priority under 35 U.S.C. § 119 to Japanese Patent Application No. 2005-130795, files on Apr. 28, 2005, which is incorporated herein by reference.

BACKGROUND OF THE INVENTION

1. Field of the Invention

The present invention relates to a process for producing 2,3,3',4'-biphenyltetracarboxylic dianhydride which is useful as a raw material for polyimide; particularly to a process for producing efficiently the powder product of high purity from a reaction mixture formed by a dimerization reaction of an o-phthalic acid diester.

2. Description of the Related Art 3,4,3',4'-Biphenyltetracarboxylic dianhydride (hereinafter, may be abbreviated as s-BPDA) and 2,3,3',4'-biphenyltetracarboxylic dianhydride (hereinafter, may be abbreviated as a-BPDA) are each known as a monomer raw material for production of aromatic polyimide. In particular, a polyimide produced from s-BPDA as a monomer component is superior in properties such as heat resistance, electrical insulation, film strength, film dimensional stability, solvent resistance and the like. Accordingly, because of a high demand for s-BPDA, an efficient process for producing a high purity s-BPDA has been intensively investigated. However, as to a-BPDA, there is no known process for producing a high purity product efficiently. Further, even if polymerized with the same aromatic diamine, a-BPDA and s-BPDA produce polyimides having entirely different properties. Hence, as to a-BPDA, a high-purity product containing no s-BPDA is needed.

For example, JP-B-1994-2715 (patent literature 1), discloses a process which comprises removing unreacted monomers and high-boiling products from a reaction product mixture of a dimerization reaction of an o-phthalic acid diester, and then subjecting the resulting mixture to a crystallization operation in an alcohol solvent such as methanol or the like, thereby high-purity 3,4,3',4'-biphenyltetracarboxylic acid tetraester (hereinafter, may be abbreviated as s-BPTT) is obtained by the isolation from its isomer, i.e. 2,3,3',4'-biphenyltetracarboxylic acid tetraester (hereinafter, may be abbreviated as a-BPTT). s-BPTT can be converted into s-BPDA by being heated in the presence of concentrated sulfuric acid in a water-free state, as described in, for example, JP-B-1994-96570 (patent literature 2). In the patent literature 1, however, there is no description on a process for obtaining high-purity a-BPDA from a by-product, a-BPTT.

With respect to the process for obtaining a 2,3,3',4'-biphenyltetracarboxylic acid tetraester (a-BPTT) as a main product, there is, in JP-A-2003-113143 (patent literature 3), a description that a reaction mixture of high a-BPTT/s-BPTT ratio can be obtained by dimerization of an o-phthalic acid diester in the presence of a particular catalyst. In the literature, there is further described that a-BPDA can be obtained by hydrolyzing a-BPTT and then heating the hydrolyzate at a high temperature for dehydration thereof; however, there is no specific description on the process for obtaining this a-BPDA.

LIST OF REFERENCES

Patent literature 1: JP-B-1994-2715
Patent literature 2: JP-B-1994-96570
Patent Literature 3: JP-A-2003-113143

SUMMARY OF THE INVENTION

It was found by the investigation by the present inventor that, when a-BPDA of insufficient purity has been reacted with another co-monomer (i.e. diamine), the resulting polyamic acid has low polymerization degree and the polyimide obtained by imidization of the polyamic acid is inferior in properties. Thus, it is extremely important to increase the purity of a-BPDA. In particular, it is extremely important from an industrial standpoint to obtain high-purity a-BPDA efficiently in the process starting from the dimerization reaction of an o-phthalic acid diester. It is also extremely important from an industrial standpoint to obtain a-BPDA in powder form efficiently.

The present invention has been made in view of the above problem. An objective of the present invention is to provide a process for producing high-purity 2,3,3',4'-biphenyltetracarboxylic dianhydride (a-BPDA) which is suitable for production of a high-molecular polyamic acid. Also, an embodiment of the present invention aims at providing a process for producing high-purity a-BPDA efficiently from a reaction product mixture of the dimerization reaction of an o-phthalic acid diester.

Aspects of the present invention are directed to the following items.

1. A process for producing 2,3,3',4'-biphenyltetracarboxylic dianhydride in powder form, comprising a step of dehydrating 2,3,3',4'-biphenyltetracarboxylic acid in an inert gas atmosphere under heating at 180 to 195° C. for sufficient time to complete dehydration.

2. A process as described in the above item 1, wherein, prior to the dehydration under heating, the water content of 2,3,3',4'-biphenyltetracarboxylic acid is reduced to 10% or less.

3. A process for producing 2,3,3',4'-biphenyltetracarboxylic dianhydride in powder form, which comprises a crystallization step of subjecting an organic solvent solution of a reaction product mixture containing 2,3,3',4'-biphenyltetracarboxylic acid tetraester, to a crystallization operation to obtain crystals of 2,3,3',4'-biphenyltetracarboxylic acid tetraester having a purity of 95% or higher, a step of hydrolyzing the crystals to obtain 2,3,3',4'-biphenyltetracarboxylic acid, and a step of dehydrating the 2,3,3',4'-biphenyltetracarboxylic acid by heating to obtain 2,3,3',4'-biphenyltetracarboxylic dianhydride, wherein the 2,3,3',4'-biphenyltetracarboxylic dianhydride obtained, when polymerized with 4,4'-diaminodiphenyl ether at equal moles at a monomer concentration of 10% by mass at 25° C. for 4.5 hours in a N-methylpyrrolidone solvent, gives a polyamic acid showing a logarithmic viscosity of 1.0 or larger as measured for a 0.5 g/100 ml N-methyl-2-pyrrolidone solution at 30° C.

4. A process as described in the above item 3, wherein after reducing the water content of 2,3,3',4'-biphenyltetracarboxylic acid to 10% or less, the dehydration step is carried out by heating at 180 to 195° C. in an inert gas atmosphere using a Henschel mixer for sufficient time to complete dehydration.

5. A process as described in the above item 3 or 4, wherein the crystallization step comprises:

a first crystallization sub-step of obtaining crystals of a 2,3,3',4'-biphenyltetracarboxylic acid tetraester having a purity of 95% or higher, a sub-step of dissolving the crystals in an organic solvent, and a second crystallization sub-step of obtaining crystals of a 2,3,3',4'-biphenyltetracarboxylic acid tetraester having a higher purity.

6. A process as described in any of the above items 3 to 5, wherein the hydrolysis is carried out under applied pressure with heating, using neither acid nor alkali.

7. A process as described in the above item 6, wherein the hydrolysis is carried out under the conditions of a temperature of 150 to 250° C. and a pressure of 0.2 to 3 MPa.

8. A process as described in the above item 6 or 7, wherein, after the hydrolysis, crystallization is carried out to obtain crystals of 2,3,3',4'-biphenyltetracarboxylic acid.

9. A process as described in any of the above items 3 to 8, wherein the reaction product mixture is obtained from reaction product of a dimerization reaction of an o-phthalic acid diester.

10. A process as described in any of the above items 3 to 9, wherein the content of 2,3,3',4'-biphenyltetracarboxylic acid tetraester in reaction product mixture is 10 to 95% by mass and the ratio of 3,4,3',4'-biphenyltetracarboxylic acid tetraester/2,3,3',4'-biphenyltetracarboxylic acid tetraester is 0.5/1 or less.

11. A process as described in any of the above items 1 to 10, wherein the content of impurities in 2,3,3',4'-biphenyltetracarboxylic dianhydride is 0.6% by mass or less.

12. A process as described in any of the above items 1 to 10, wherein the content of iron in 2,3,3',4'-biphenyltetracarboxylic dianhydride is 1 ppm or less.

13. A process as described in any of the above items 1 to 12, wherein a median particle size of the powder of 2,3,3',4'-biphenyltetracarboxylic dianhydride is 100 µm or less.

14. A process as described in any of the above items 1 to 12, wherein a median particle size of the powder of 2,3,3',4'-biphenyltetracarboxylic dianhydride is 50 µm or less.

According to the present invention, there can be provided a process for producing high-purity 2,3,3',4'-biphenyltetracarboxylic dianhydride (a-BPDA) which is suitable for production of a high-molecular polyamic acid.

According to an aspect of the present invention, high-purity 2,3,3',4'-biphenyltetracarboxylic dianhydride (a-BPDA) can be produced efficiently from a reaction product mixture of the dimerization reaction of an o-phthalic acid diester.

As described later, the present invention is particularly suitable for producing a-BPDA in the form of powder.

DETAILED DESCRIPTION OF THE PREFERRED EMBODIMENT

The main abbreviations used in the present invention are as follows.

BPTT: 2,3,3',4'-biphenyltetracarboxylic acid tetraester
s-BPTT: 3,4,3',4'-biphenyltetracarboxylic acid tetraester
a-BPTA: 2,3,3',4'-biphenyltetracarboxylic acid
s-BPTA: 3,4,3',4'-biphenyltetracarboxylic acid
a-BPDA: 2,3,3',4'-biphenyltetracarboxylic dianhydride
s-BPDA: 3,4,3',4'-biphenyltetracarboxylic dianhydride In the following description, each two types of nomenclatures may be mentioned together as necessary.

An aspect of the present invention comprises (1) a step of obtaining a reaction product mixture (a crude dimer) containing a-BPTT,
(2) a crystallization step for a-BPTT,
(3) a hydrolysis step, and
(4) a dehydration step.

They are described below on a typical continuous process as an example.

Production of Reaction Product Mixture (Crude Dimer)

The reaction product mixture containing a-BPTT (2,3,3',4'-biphenyltetracarboxylic acid tetraester), fed to the next crystallization step is obtained by appropriately treating a reaction mixture obtained from the dimerization reaction of an o-phthalic acid diester derived from an alcohol having about 1 to 5 carbon atoms. Incidentally, since a-BPTT is a dimer of an o-phthalic acid diester, the reaction mixture product is expressed as "reaction product mixture (crude dimer)", in some cases.

This step is described with reference to the flow chart of FIG. 1. The dimerization reaction (S1) of o-phthalic acid diester is known in the art. For example, the reaction system is heated in the presence of a catalyst containing a bi-valent palladium salt, preferably in the absence of a solvent while a gas containing molecular oxygen is being fed thereinto. The reaction product mixture ordinarily contains a-BPTT, s-BPTT, unreacted o-phthalic acid diester, and by-products such as biphenyltricarboxylic acid derivative (triacid component), trimer, resinous substance and the like.

In an ordinary operation, the catalyst residue is removed from the reaction mixture by filtration or the like (S2); then, distillation (S3) is carried out to remove low-boiling components and high-boiling components. The low-boiling components are composed mainly of an unreacted o-phthalic acid diester. Since the unreacted o-phthalic acid diester dissolves biphenyltetracarboxylic acid tetraesters (s-type and a-type), the distillation is preferred to be carried out so that the content of o-phthalic acid diester becomes 1.0% or less. The recovered o-phthalic acid diester is reused. Distillation is continued to take a distillate containing a-BPTT and s-BPTT, out of the system. By this operation, high-boiling products such as trimer, resinous substance and the like are removed. When the distillation operation is carried out continuously, at least two times of, as necessary three times of distillation operations are carried out using a plurality of distillation apparatuses.

The mixture remaining after removal of the low-boiling components and the high-boiling components contain at least a-BPTT and s-BPTT. The ratio of a-BPTT and s-BPTT differs depending upon the kind of the dimerization catalyst used, the reaction conditions employed, etc. When a-type is obtained as a by-product from the process for obtaining s-type as a main product, the reaction mixture contains s-BPTT in a large amount. The s-BPTT is crystallized and removed from the mixture (S4). The crystallization operation of s-BPTT can be carried out according to the crystallization operation of a-BPTT which will be described later. The s-BPTT obtained is used per se as a raw material for s-BPDA which is a raw material for polyimide. In the next distillation operation (S5), the solvent is recovered from the mother liquor of crystallization; then, the distillation residue is subjected to a rectification operation (S6) to separate low-boiling components containing a-BPTT by distillation. Since the bottom product of the distillation (rectification) contains s-BPTT, s-BPTT is recovered therefrom.

In the continuous process described herein, the distillate from the rectification operation (S6) becomes a "reaction product mixture (crude dimer)" to be fed to the next a-BPTT crystallization step. Besides a-BPTT, the distillate contains s-BPTT, 2,3,3',4'-biphenyltetracarboxylic acid triester, 3,4,3', 4'-biphenyltetracarboxylic acid triester and the like. In order to carry out a crystallization operation efficiently in the next a-BPTT crystallization step, the content of a-BPTT relative to the total amount of the distillate is preferably 30% by mass or more, more preferably 35% by mass or more, particularly preferably 40% by mass or more. While the content of a-BPTT is preferred to be as high as possible, it is generally 95% by mass or less.

In addition, if s-BPTT is present in a large amount in the distillate, crystallization of s-type compound takes place in the next crystallization step for a-type compound; therefore, the amount of s-type is preferred to as small as possible. The s-type/a-type ratio is less than 1/1, preferably 0.5/1 or less, more preferably 0.2/1 or less.

A reaction product mixture (crude dimer) having such a composition is fed to the next a-BPTT crystallization step. The reaction product mixture fed to the next step is not restricted only to one obtained in the above-mentioned process, as long as it is in the above compositional range.

That is, in the above, there has been described a case in which the content of s-type is high in the BPTTs (biphenyltetracarboxylic acid tetraesters) obtained by the dimerization reaction. However, the s-type/a-type ratio after the dimerization reaction differs depending upon the catalyst used, the reaction conditions employed, and the like. Thus, the treatment procedure after the dimerization reaction may be changed depending upon the composition of the reaction mixture after the dimerization reaction.

For example, when the content of a-BPTT is high, low-boiling components and high-boiling components are removed by distillation (S3), after the dimerization reaction; then, without carrying out s-type crystallization, a rectification operation (S6) may be carried out to obtain a "reaction product mixture (crude dimer)" containing a-BPTT as main component. Further, when the a-type/s-type ratio of the BPTTs obtained by the dimerization reaction is large, high-boiling components and low-boiling components are removed in the distillation operation (S3) and the remaining mixture may be used as a "reaction product mixture (crude dimer)", in the next a-BPTT crystallization step.

a-BPTT Crystallization Step

Next, the reaction product mixture (crude dimer) is subjected to crystallization and the crystals of a-BPTT formed are taken out. That is, a crystallization solvent is added to the reaction product mixture (crude dimer) to prepare a solution, and a-BPTT is allowed to separate out as crystals from the solution. The purity of the a-BPTT crystals taken out is preferably 95% or higher, particularly preferably 98% or higher, most preferably 99% or higher. Such a purity can be achieved by setting the step conditions appropriately.

Figure 2:
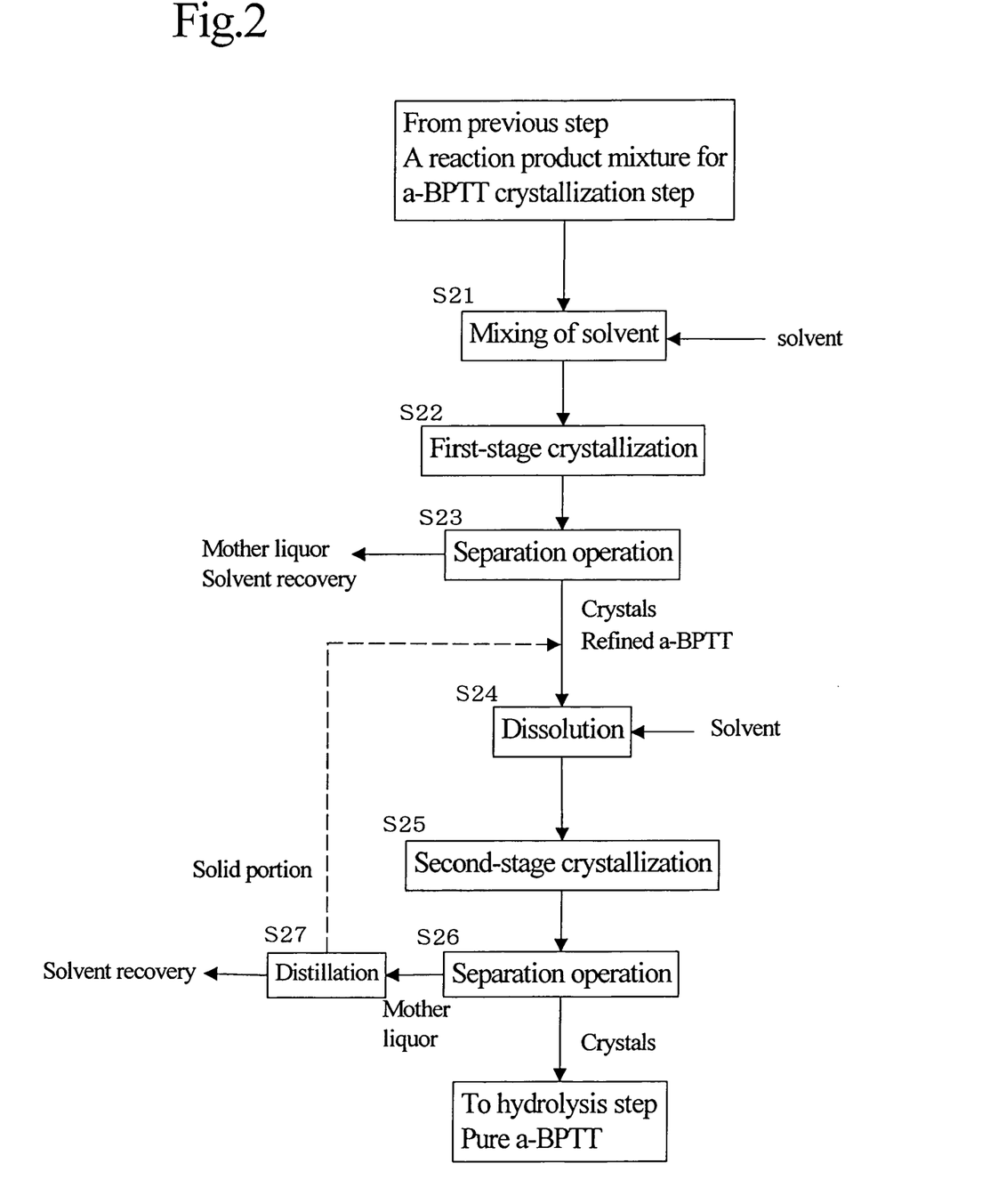
FIG. 2 is a flow chart showing a step for obtaining pure a-BPTT from a reaction product mixture containing a-BPTT, by two-stage crystallization.

An embodiment of the crystallization step is described on a case of continuous two-stage crystallization, referring to the flow chart of FIG. 2.

In a continuous operation, the reaction product mixture (crude dimer) is sent in a line and mixed with a crystallization solvent (S21). When the reaction product mixture (crude dimer) is a distillate from the distillation operation, it is sent continuously at a relatively high temperature (for example, about 100 to 140° C.); therefore, the crystallization solvent is heated as necessary and added or the mixture after solvent addition is heated to make the mixture a solution.

Then, the solution is introduced into a first-stage crystallization apparatus (S22). The crystallization apparatus is, for example, a crystallization tank of mixing tank type. The average residence time of the slurry (i.e. mixture of crystal and liquid) in the tank is determined by the volume of remaining in-tank slurry, the amount of solution fed and the amount taken out. The crystallization tank is cooled so as to keep a given crystallization temperature; when the solution containing a-BPTT is introduced into the crystallization tank, the solution is immediately cooled by the in-tank slurry in the crystallization tank and crystallization takes place. After crystallization, crystal-liquid-mixture remains in the tank as an in-tank slurry and then is sent to the next separation operation (S23).

The crystal-containing slurry is separated into crystals and a mother liquor by, for example, a centrifuge, in a separation operation (S23). The crystals obtained are preferred to have a purity of 95% or higher, particularly 98% or higher and are used as refined a-BPTT in second-stage crystallization.

Next, a solvent is added to the refined a-BPTT, followed by heating for dissolution (S24). Then, second-stage crystallization is carried out (S25). The crystals formed are separated (S26) to obtain high-purity (preferably about 99% or higher) a-BPTT.

The crystallization apparatus and operation and the separation apparatus and operation may be the same as in the first-stage crystallization/separation operation. In addition, the mother liquor after separation of crystals may be subjected to distillation (S27) to recover a solvent for recycling, and the residual solid portion may be combined with the refined a-BPTT for reuse in the second-stage crystallization.

In the above crystallization operation, the crystallization solvent may be organic solvents including lower alcohols of 1 to 6 carbon atoms, such as methanol, ethanol, propanol, butanol, pentanol, hexanol and the like, and ether, tetrahydrofuran, toluene, methyl cellosolve, nitrobenzene, chloroform, carbon tetrachloride, acetone, methyl acetate, ethanol-ether mixture and the like. Particularly, lower alcohols having 1 to 4 carbon atoms, which are the same alcohols as those providing alkoxy groups in the BPTT, are preferred and methanol is preferred most.

The proportion of the crystallization solvent added and the conditions such as crystallization temperature and the like can be appropriately determined in consideration of the solvency of the solvent.

With respect to the ratio of the target mixture for crystallization {in the above case, the reaction product mixture (crude dimer) or refined a-BPTT} and the crystallization solvent, the crystallization solvent relative is used in the volume ratio of, for example, at least 1/1, preferably at least 2/1 relative to the target mixture; and when the amount of the treatment is considered, ordinarily 500/1 or less, preferably 100/1 or less.

When the crystallization solvent is an alcohol (most preferably methanol), the alcohol is used in the volume ratio of ordinarily 1/1 to 100/1, preferably 1/1 to 30/1, particularly preferably 2/1 to 20/1, most preferably 2/1 to 10/1 relative to the target mixture.

When two-stage crystallization is carried out as in the above case, it is also preferred that the proportion of the solvent is larger in the second stage than in the first stage.

The reaction product mixture (crude dimer)/solvent ratio in the first stage is preferably 1/1 to 1/100, particularly preferably 1/1 to 1/20, especially 1/2 to 1/10, most preferably 1/2 to 1/7; and the refined a-BPTT/solvent ratio in the second stage is preferably 1/1 to 1/30, particularly preferably 1/2 to 1/20, most preferably 1/3 to 1/10. In a typical case of using a lower alcohol, the ratio in the first stage is 1/1.5 to 1/7 (especially 1/2 to 1/7) and the ratio in the second stage is 1/2.5 to 1/10 (especially 1/3 to 1/10).

The solution temperature before cooling and the crystallization temperature (cooling temperature) can be appropriately determined according to the solvent used. The crystallization temperature (cooling temperature) is preferably 0 to 80° C., more preferably 10 to 60° C. from the standpoint of operation. When an alcohol (most preferably methanol) is used as the crystallization solvent, the crystallization temperature is preferably 10 to 60° C., more preferably 20 to 50° C., most preferably 25 to 50° C. In a typical case of carrying out two-stage crystallization as in the above embodiment, the first-stage crystallization temperature is 10 to 50° C. and the second-stage crystallization temperature is 20 to 60° C. Preferably, the second-stage temperature is made higher than the first-stage temperature.

The solution temperature before crystallization is preferred to be higher than the crystallization temperature by generally at least 10° C. (temperature difference), particularly by at least 15° C. and is preferred to be practically not higher by more than 80° C. (temperature difference), particularly not higher by more than 60° C. (temperature difference). Typically, the temperature difference is preferred to be higher by about 15 to 40° C.

In the above embodiment, a case of two-stage crystallization has been described. However, one-stage crystallization or multi-stage crystallization of three or more stages (for example, three to five stages) may be employed. However, in one-stage crystallization, it is ordinarily often difficult to obtain a sufficient purity. Since a practical purity is obtained ordinarily by two stages by setting the crystallization conditions appropriately, there is substantially no merit of employing three or more stages.

The crystallization operation using a crystallization tank of mixing tank type has been described above. However, any apparatus may be used and both continuous operation and batch operation may be used. For example, when batch operation is conducted, a solution for crystallization is fed into a crystallization tank and is gradually cooled to a crystallization temperature, seed crystals are added as necessary, and crystals are allowed to separate out. In an example, in the first-stage crystallization, a 60° C. solution for crystallization is gradually cooled; when a crystallization temperature (for example, 25° C.) has been reached, seed crystals are added to allow crystals to precipitate; aging is conducted for about 1 to 10 hours; then, the crystals are separated. Subsequently, in the second stage, a solvent is added to the crystals obtained in the first stage and the crystals are dissolved at, for example, 60° C.; the resulting solution is gradually cooled; seed crystals are added at about 50° C. to allow crystals to precipitate; aging is conducted at about 30 to 45° C. for about 1 to 10 hours; then, the crystals are separated.

The separation operation is not restricted to centrifugation. Separation by filtration, for eaxample, may be also used.

Hydrolysis Step

The hydrolysis step (see FIG. 3) is a step of hydrolyzing the high-purity a-BPTT (2,3,3',4'-biphenyltetracarboxylic acid tetraester) obtained in the crystallization step, to obtain high-purity a-BPTA (2,3,3',4'-biphenyltetracarboxylic acid).

Figure 3:
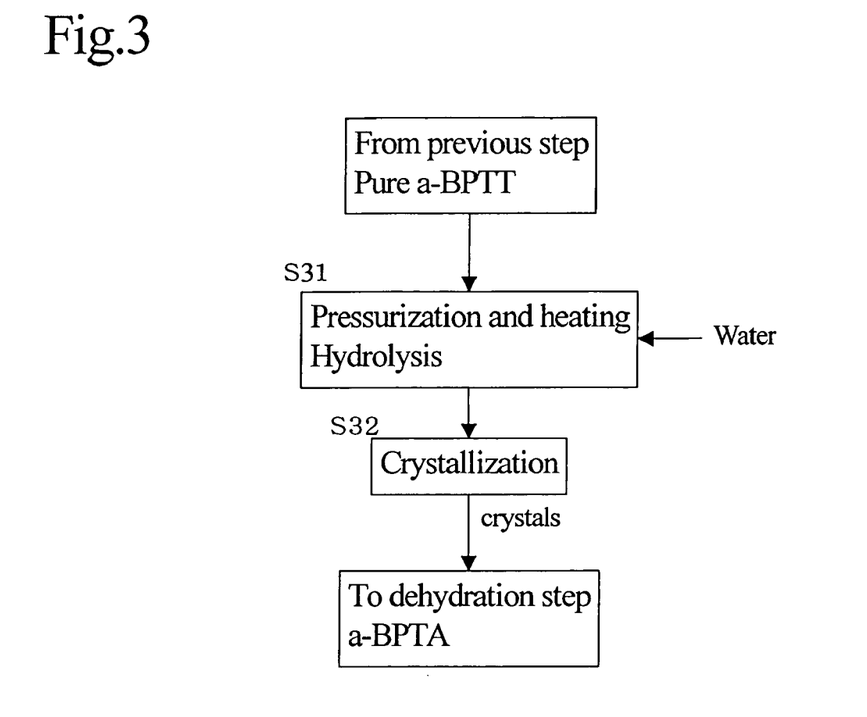
FIG. 3 is a flow chart showing a step for obtaining a-BPTA from pure a-BPTT.

A known hydrolysis method may be employed. In the present invention, however, there is preferred a hydrolysis method wherein neither acid nor alkali is added, preferably only pure water is added, and hydrolysis is allowed to take place under applied pressure under heating preferably while an alcohol is being distilled off (S31). In this method, since no impurity (e.g. acid or alkali) is added, high-purity a-BPTA can be obtained.

Specifically, the pure a-BPTT obtained in the above crystallization step and pure water are fed into a reaction vessel at a volume ratio of, for example, 1/1 to 1/10; there are selected a reaction temperature of, for example, 150 to 250° C. and a pressure of, for example, 0.2 to 3 MPa; while pure water is being fed into the reaction vessel, nearly the equivalent volume is distilled off from the gas phase of reaction, where the alcohol eliminated from the ester is removed from the reaction system simultaneously. The total amount of pure water fed is not particularly restricted but is, for example, 5 to 30 times, particularly 6 to 15 times the amount of pure a-BPTT fed.

After the hydrolysis, the recovery of a-BPTA from the aqueous solution is conducted preferably by crystallization (S32). For example, after the completion of the reaction, cooling is made in a crystallization tank; seed crystals are added at, for example, 50° C. and the system is maintained at 40° C.; then, centrifugation is conducted to separate and obtain crystals of a-BPTA. By obtaining a-BPTA by crystallization, impurities such as s-BPTA and the like are further reduced and a-BPTA of extremely high purity can be obtained.

In the above series of steps, a high-purity a-BPTT can be obtained by the crystallization step for a-BPTT and even higher purity a-BPTA can be obtained by the hydrolysis using neither acid nor alkali and the crystallization. Since a raw material of such high purity can be sent to the next dehydration step, final a-BPDA can have an enhanced purity.

Dehydration Step

The next dehydration step (FIG. 4) is a step wherein a-BPTA (2,3,3',4'-biphenyltetracarboxylic acid) is dehydrated to obtain a-BPDA (2,3,3',4'-bihenyltetracarboxylic dianhydride). According to the investigation by the present inventor, when the purity (including the dehydration degree) of the a-BPDA obtained is low, the polyamic acid, further polyimide produced from the a-BPDA are inferior in properties.

Figure 4:
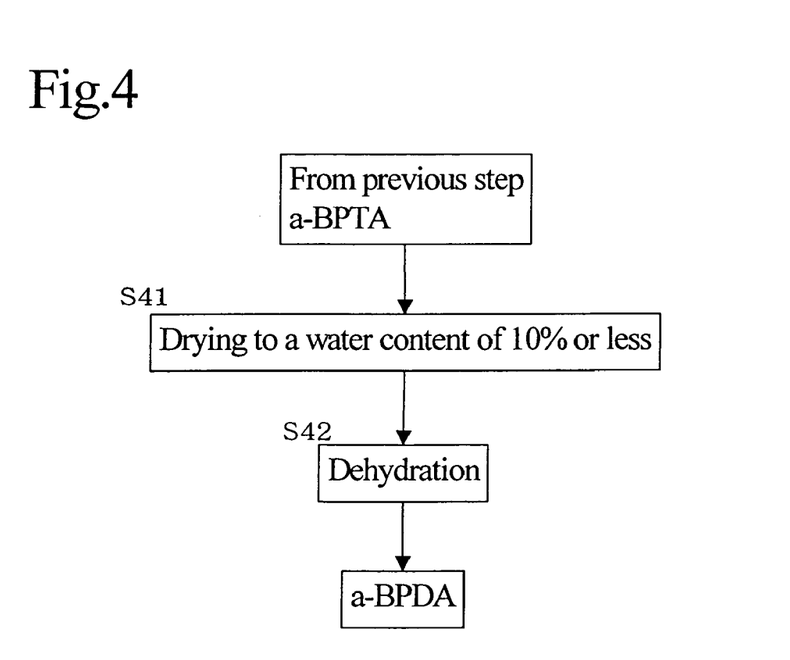
FIG. 4 is a flow chart showing a step for obtaining a-BPDA from a-BPTA.

In the present invention, it is preferred to first dry a-BPTA sufficiently before its dehydration to reduce its water content. When the water content of a-BPTA before its dehydration is high, the polyamic acid and further the polyimide both obtained from a-BPDA are inferior in properties. The reason is not clarified but is considered to be due to a low dehydration degree of a-BPDA. In the present invention, it is preferred to dry a-BPTA so that its water content is reduced to 10% or less, particularly 5% or less (S41). More preferably, the water content is reduced to 4.5% or less, particularly 4% or less.

The a-BPTA obtained in the previous step by hydrolysis and subsequent crystallization can be allowed to have a reduced water content of 10% or less, particularly 5% or less, for example, by drying at 50 to 180° C. at normal pressure or under reduced pressure using a mixer for preferably about 1 to 20 hours.

Then, the dehydration of a-BPTA with heating (S42) is carried out in an inert gas atmosphere, preferably in a nitrogen gas stream, at a temperature of 180 to 195° C., preferably 185 to 195° C. When the heating temperature is low, the a-BPDA obtained gives a polyamic acid and consequently a polyimide both inferior in properties. This is considered to be mainly due to insufficient dehydration. When the heating temperature is too high, there are generated a large amount of impurities including triacid components (e.g. derivatives such as biphenyltricarboxylic monoanhydride and the like.) produced as by-products by decarboxylation, and there arises a problem in that the a-BPDA obtained gives a low molecular-weight polyamic acid and a resulting polyimide. The time of heating can be set appropriately and the heating can be carried out, for example, for 2 to 30 hours, preferably for 2 to 20 hours. In a typical case, heating is carried out at 195° C. for 2 to 15 hours.

Heating for dehydration of a-BPTA is preferably carried out using a Henschel mixer while mixing crystals a-BPTA and subsequent a-BPDA. The Henschel mixer is preferably operated at the number of revolutions of about 100 to about 500 rpm, particularly about 200 to about 400 rpm. The heating temperature employed herein is an average temperature measured by a contact thermocouple. The heating is controlled and carried out by heating medium and the number of revolutions of the Henschel mixer.

Throughout the procedure of drying and dehydration in the present invention, a-BPTA and resulting a-BPDA are preferably kept in the form of powder, generally powder of crystals.

The operation from drying to dehydration may be carried out in a series. For example, after the drying, the temperature of the system is increased gradually and the system is kept in the above-mentioned given dehydration temperature range for a given period of time.

The a-BPDA obtained as above is a white powder of high purity. By using this as a raw material, there can be obtained a polyamic acid of high molecular weight and further a polyimide superior in heat resistance and mechanical properties. A high-purity a-BPDA can be produced at high productivity by using, in particular, a process which comprises in series:

(1) conducting a crystallization operation to obtain a-BPTT crystals having a purity of 95% or higher (preferably 98% or higher, particularly 99% or higher),
(2) heating the crystals under applied pressure preferably using neither acid nor alkali, to give rise to hydrolysis,
(3) obtaining a-BPTA preferably by crystallization and sending it to a dehydration step,
(4) reducing the water content of the a-BPTA preferably to 10% or less, particularly to 5% or less, and
(5) conducting dehydration under heating.

By using this a-BPDA as a raw material, there can be obtained a polyamic acid of high molecular weight and consequently a polyimide superior in heat resistance and mechanical properties. By using a-BPDA produced by the present invention, there can be easily obtained a polyamic acid of high molecular weight; that is, a polyamic acid obtained from the a-BPDA under standard conditions (described later) shows a logarithmic viscosity η of 1 or more, preferably 1.2 or more, particularly 1.3 or more.

Further, in the production process of the present invention, there can be easily obtained a-BPDA having an impurity content of 0.6% or less, particularly in powder form. The impurities mentioned here are components other than a-BPDA and a-BPTA, and the impurities contained under ordinary conditions include a large amount of triacid components, for example, biphenyltricarboxylic acid derivatives such as biphenyltricarboxylic monoanhydride and the like; high-molecular compounds; and so forth. According to an aspect of the present invention, high-purity a-BPDA particularly in powder form having an iron content of 1 ppm or less can be obtained easily. Preferably, a-BPDA powder obtained according to the present invention has median particle size of about 100 μm or less, particularly about 50 μm or less, and hence exhibits good processability to obtain polyamic acid composition.

EXAMPLES

Next, the present invention will be described in more details with reference to Examples.

Method for Measurement of Logarithmic Viscosity (η) of Polyamic Acid

"Polyamic acid obtained under standard conditions" refers to a polyamic acid obtained by polymerizing a-BPDA and 4,4'-diaminodiphenyl ether at equal moles at a monomer concentration of 10% by mass in a N-methylpyrrolidone solvent at 25° C. for 4.5 hours. In each Example and Comparative Example, a sample a-BPDA was polymerized under the standard conditions to obtain a polyamic acid. A solution of the polyamic acid (a 0.5 g/100 ml N-methyl-2-pyrrolidone solution) is prepared; the time (t1) taken for the solution to pass between the upper line and the lower line of a Cannon-Fenske viscometer at 30° C. is measured; subsequently, the time (t0) taken for the solvent alone to pass is measured. The logarithmic viscosity (η) of the polyamic acid is expressed by the following expression.

Logarithmic viscosity=$\{\ln(t1/t0)\}$/solution viscosity (wherein, ln denotes natural logarithm.)

<Method for measurement of particle size>

The size of the a-BPDA powder was analysed using Laser diffraction/scattering particle size distribution measuring instrument (Model: LA-910, product of Laboratories Co., Ltd.) and using water as dispersing medium for dispersion with ultrasonic wave.

Example 1

A dimerization reaction of dimethyl o-phthalate was carried out using a catalyst having a composition of palladium acetate/o-phenanthroline/copper acetate=2/2/0.5 (molar ratio). The reaction mixture was subjected to a plurality of times of distillation to remove low-boiling components and high-boiling components; s-BPTT was removed by crystallization using methanol as a crystallization solvent; the methanol was removed by distillation; rectification was conducted to obtain, as a distillate, a reaction product mixture (crude dimer, s-type/a-type=0.1/1) containing about 40% of a-BPTT (in this case, tetramethyl 2,3,3',4'-biphenyltetracarboxylate).

The reaction product mixture as a distillate was at about 120° C. In a line, to 120 L/H (litter/hours) of the reaction product mixture (crude dimer) was mixed in line and 420 L/H of methanol heated to 50° C. The resulting mixture was continuously fed into a crystallization tank controlled at 25° C. where residence time was about 8 hours from outside.

This results in precipitation of a-BPTT crystal. An in-tank solution containing crystals was withdrawn from the crystallization tank and sent to a centrifuge for separation into crystals and a mother liquor. The a-BPTT crystals obtained had a purity of 98.5% and a yield of 40%.

To 120 L/H of the 98.5% refined a-BPTT was added 600 L/H of methanol; the a-BPTT was dissolved with heating; the resulting solution was fed into a crystallization tank controlled at 40° C. so that the residence time was about 6 hours. Thus, continuous crystallization was carried out.

The in-tank solution containing the crystals formed was sent to a centrifuge to separate the crystals. The crystals obtained had a purity of 99.5% and a yield of 50%.

1,000 liters of the 99.5% pure a-BPTT obtained and 3,000 liters of pure water were mixed in a reaction vessel and a hydrolysis reaction was carried out at a reaction temperature of 200° C. at a pressure of 1.5 to 2.0 MPa for 48 hours with pure water being fed at a rate of 300 L/H. The hydrolyzate mixture obtained was cooled to 50° C. and seed crystals were added to give rise to crystallization. The mixture containing the crystals formed was sent to a centrifuge and centrifugation was carried out at 40° C. to separate the crystals. The a-BPTA crystals obtained had a purity of 99.7% and a yield of 100%.

The a-BPTA crystals were dried at 150° C. for 3 hours to obtain a-BPTA having a water content of 5% or less. This a-BPTA was dehydrated at 195° C. for 6 hours in a nitrogen stream using a heating apparatus equipped with a Henschel mixer (operated at 300 to 350 rpm), to obtain a white powder of a-BPDA. During 9 hours of the above drying and dehydration oeration, a-BPTA and a-BPDA were kept in the form of powder of crystals. This a-BPDA (overall yield: 20%) was evaluated by liquid chromatography. As a result, the percentage purity of the a-BPDA was 99.7%. The polymer (polyamic acid) using the a-BPDA and diaminodiphenyl ether showed a logarithmic viscosity ($\eta$) of 1.4. The a-BPDA had an iron content of 0.1 ppm.

Example 2

Dimethyl o-phthalate was subjected to a dimerization reaction using, as a dimerization catalyst, a catalyst having a composition of palladium acetate/copper acetate=2/20 (molar ratio). The reaction mixture was subjected to a plurality of times of distillation to remove low-boiling components and high-boiling components. Then, rectification was carried out to obtain, as a distillate, a reaction product mixture (a crude dimer) containing about 70% of a-BPTT.

Then, under the same conditions as in Example 1, two-stage crystallization was carried out to obtain pure a-BPTT, followed by hydrolysis and dehydration to obtain a white powder of a-BPDA (overall yield: 27.5%). Incidentally, except that the yield of a-BPTT in the first-stage crystallization was 55%, other purities and the logarithmic viscosity of polyamic acid were the same as in Example 1.

Example 3

A white powder of a-BPDA was obtained in the same manner as in Example 1 except that the residue after distillation of methanol from the mother liquor of the second-stage crystallization was combined with the a-BPTT after the first-stage crystallization and the mixture was used as a raw material for second-stage crystallization. As a result, the overall yield increased to 36% and the purity was 99.7%. The logarithmic viscosity ($\eta$) of a polymer (a polyamic acid) between the a-BPDA and diaminodiphenyl ether was 1.4.

Example 4

A white powder of a-BPDA was obtained in the same manner as in Example 1 except that dehydration was conducted after the completion of first-stage crystallization and then dehydration was conducted. The overall yield was increased to 39%; however, the purity was 98.5% and a polymer (polyamic acid) between the a-BPDA and diaminodiphenyl ether showed a logarithmic viscosity of ($\eta$) of 1.15.

Each a-BPDA obtained in Examples 2 to 4 had an iron content of 0.1 ppm. Further, each a-BPDA powder of Examples 1 to 4 has a median particle size of 39 µm, as analyzed by laser diffraction/scattering method.

Comparative Example 1 a-BPDA was obtained in the same manner as in Example 1 except that the temperature of dehydration was 170° C. The purity (total of a-BPTA and/or a-BPDA) was 99.7% and a polymer (a polyamic acid) between the a-BPDA and diaminodiphenyl ether showed a logarithmic viscosity ($\eta$) of 0.2 which was extremely low.

Comparative Example 2

Using part of the a-BPTA obtained in Example 1, dehydration was carried out in a nitrogen atmosphere at 210° C. for 15 hours using a hot-air circulation type heating apparatus, to obtain a white lump of a-BPDA. This lump was then crushed and ground in a mortar to obtain white powder. However, the particle size was not uniform.

What is claimed is:

1. A process for producing 2,3,3',4'-biphenyltetracarboxylic dianhydride in powder form, comprising a step of dehydrating 2,3,3', 4'-biphenyltetracarboxylic acid in an inert gas atmosphere under heating to no more than 195° C. for sufficient time to complete dehydration;
   wherein, prior to the step of dehydrating under heating, the water content of 2,3, 3',4'-biphenyltetracarboxylic acid is reduced to 10% or less.

2. A process for producing 2,3,3',4'-biphenyltetracarboxylic dianhydride in powder form, comprising:
   a crystallization step of subjecting an organic solvent solution of a reaction product mixture containing 2,3,3',4'-biphenyltetracarboxylic acid tetraester, to a crystallization operation to obtain crystals of 2,3,3',4'-biphenyltetracarboxylic acid tetraester having a purity of 95% or higher,
   a step of hydrolyzing the crystals to obtain 2,3,3',4'-biphenyltetracarboxylic acid, and
   a step of dehydrating the 2,3,3',4'-biphenyltetracarboxylic acid by heating to a temperature not exceeding 195° to obtain 2,3,3',4'-biphenyltetracarboxylic dianhydride,
   wherein the 2,3,3',4'-biphenyltetracarboxylic dianhydride obtained, when polymerized with 4, 4'-diaminodiphenyl ether at equal moles at a monomer concentration of 10% by mass at 25° C. for 4.5 hours in a N-methylpyrrolidone solvent, gives a polyamic acid showing a logarithmic viscosity of 1.0 or larger as measured in a 0.5 g/100 ml N-methyl-2-pyrrolidone solution at 30° C., wherein after reducing the water content of 2,3, 3',4'-biphenyltetracarboxylic acid to 10% or less, the dehydration step is carried out by heating at a temperature not exceeding 195° C. in an inert gas atmosphere for sufficient time to complete dehydration.

3. The process as claimed in claim 2, wherein the dehydration step is carried out using a Hensehel mixer.

4. A process as claimed in claim 2, wherein the crystallization comprises:
   a first crystallization sub-step of obtaining crystals of a 2,3,3',4'-biphenyltetracarboxylic acid tetraester having a purity of 95% or higher,
   a sub-step of dissolving the crystals in an organic solvent, and a second crystallization sub-step of obtaining crystals of a 2,3,3',4'-biphenyltetracarboxylic acid tetraester having a higher purity.

5. A process as claimed in claim 2, wherein the hydrolysis is carried out under applied pressure with heating, using neither acid nor alkali.

6. A process as claimed in claim 5, wherein the hydrolysis is carried out under the conditions of a temperature of 150 to 250° C. and a pressure of 0.2 to 3 MPa.

7. A process as claimed in claim 5, wherein, after the hydrolysis, crystallization is carried out to obtain crystals of 2,3,3',4'-biphenyltetracarboxylic acid.

8. A process as claimed in clam 2, wherein the reaction product mixture is obtained from reaction product of a dimerization reaction of an o-phthalic acid diester.

9. A process as claimed in claim 2, wherein the content of 2,3,3',4'-biphenyltetracarboxylic acid tetraester in the reaction product mixture is 10 to 95% by mass and the ratio of 3, 4, 3', 4'-biphenyltetracarboxylic acid tetraester/2,3,3',4'-biphenyltetracarboxylic acid tetraester is 0.5/1 or less.

10. A process as claimed in claim 1, wherein the content of impurities in 2,3,3',4'-biphenyltetracarboxylic dianhydride is 0.6% by mass or less.

11. A process as claimed in claim 2, wherein the content of impurities in 2,3,3',4'-biphenyltetracarboxylic dianhydride is 0.6% by mass or less.

12. A process as claimed in claim 1, wherein the content of iron in 2,3,3',4'-biphenyltetracarboxylic dianhydride is 1 ppm or less.

13. A process as claimed in claim 2, wherein the content of iron in 2,3,3',4'-biphenyltetracarboxylic dianhydride is 1 ppm or less.

14. A process as claimed in claim 1, wherein a median particle size of the powder of 2,3,3',4'-biphenyltetracarboxylic dianhydride is 100 μm or less.

15. A process as claimed in claim 2, wherein a median particle size of the powder of 2,3,3',4'-biphenyltetracarboxylic dianhydride is 100 μm or less.

16. A process as claimed in claim 1, wherein a median particle size of the powder of 2,3,3',4'-biphenyltetracarboxylic dianhydride is 50 μm or less.

17. A process as claimed in claim 2, wherein a median particle size of the powder of 2,3,3',4'-biphenyltetracarboxylic dianhydride is 50 μm or less.

* * * * *

UNITED STATES PATENT AND TRADEMARK OFFICE
CERTIFICATE OF CORRECTION

| | | |
|---|---|---|
| PATENT NO. | : 7,417,108 B2 | Page 1 of 2 |
| APPLICATION NO. | : 11/208823 | |
| DATED | : August 26, 2008 | |
| INVENTOR(S) | : Nakayama et al. | |

Figure 1:
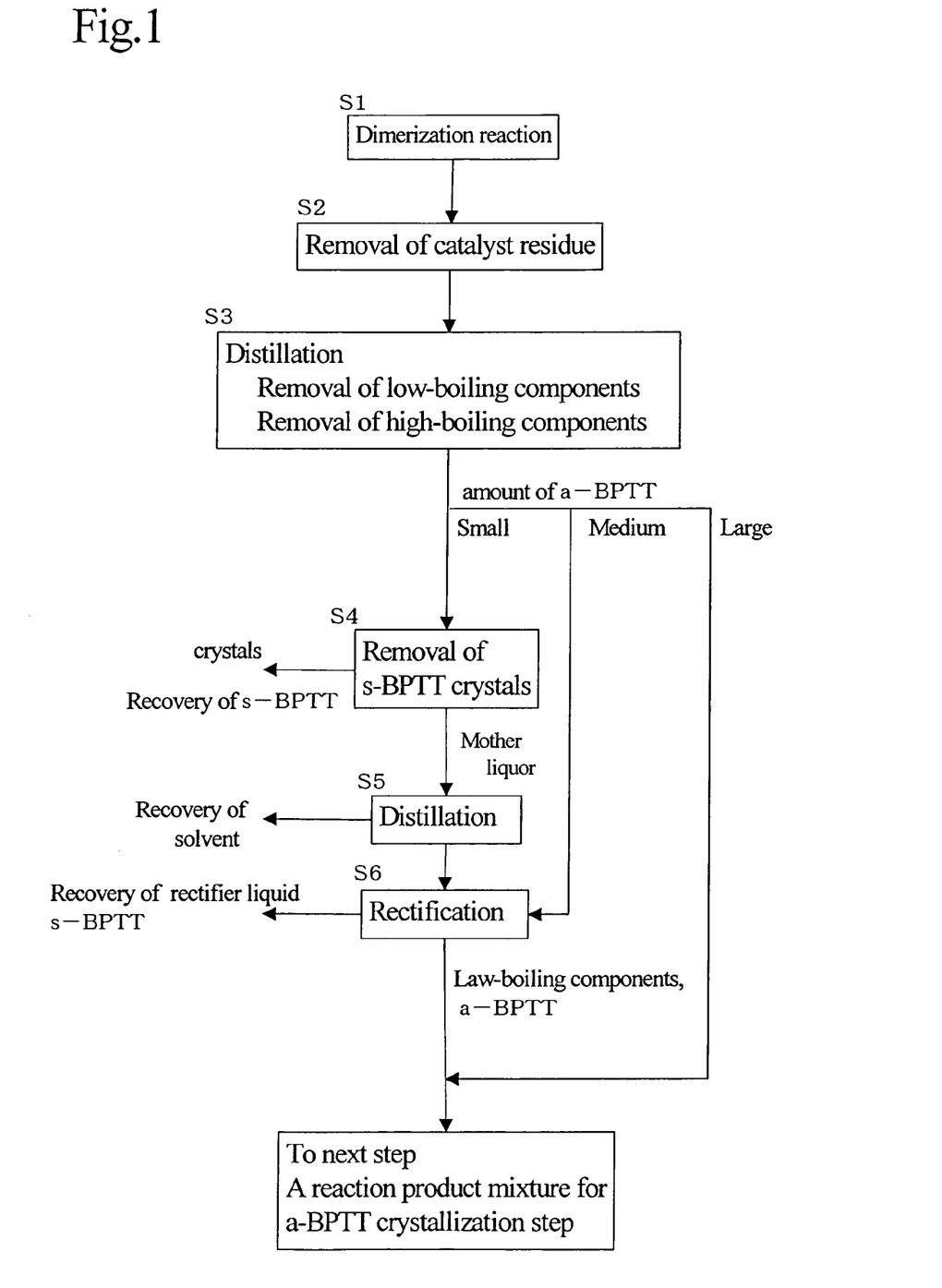
FIG. 1 is a flow chart showing a step for dimerizing an o-phthalic acid ester and obtaining a reaction product mixture containing a-BPTT.

It is certified that error appears in the above-identified patent and that said Letters Patent is hereby corrected as shown below:

In Drawings In Fig. 1, line 21 (approximately), please delete "Law" and insert -- Low --, therefor.

At Col 6, Lines 37-43, please delete "The crystallization apparatus......................second-stage crystallization." and insert the same on Col. 6, Line 36, after "a-BPTT." as a continuation of the same paragraph.

At Col 6, Lines 66-67 and Col 7, Lines 1-3, please delete "When the.................target mixture." and insert the same on Col. 6, Line 65, after "100/1 or less." as a continuation of the same paragraph.

At Col 7, Lines 7-15, please delete "The reaction........(especially 1/3 to 1/10)." and insert the same on Col. 7, Line 6, after "stage" as a continuation of the same paragraph.

At Col 7, Line 67, please delete "eaxample" and insert -- example --, therefor.

UNITED STATES PATENT AND TRADEMARK OFFICE
CERTIFICATE OF CORRECTION

PATENT NO. : 7,417,108 B2
APPLICATION NO. : 11/208823
DATED : August 26, 2008
INVENTOR(S) : Nakayama et al.

It is certified that error appears in the above-identified patent and that said Letters Patent is hereby corrected as shown below:

At Col 10, Lines 60-64, please delete "This result................yield of 40%." and insert the same on Col. 10, Line 59, after "outside." as a continuation of the same paragraph.

At Col 11, Line 22 (approx.), please delete "oeration" and insert -- operation --, therefor.

At Col 12, Line 45 (in Claim 2), please delete "195°" and insert -- 195°C --, therefor.

At Col 12, Line 60, (in Claim 3), please delete "Hensehel" and insert -- Henschel --, therefor.

Signed and Sealed this

Fourteenth Day of July, 2009

JOHN DOLL
*Acting Director of the United States Patent and Trademark Office*